United States Patent [19]

Bennett

[11] Patent Number: Plant 5,518

[45] Date of Patent: Jul. 23, 1985

[54] MINIATURE ROSE PLANT

[76] Inventor: Cecelia L. D. Bennett, 489 Minot Ave., Chula Vista, Calif. 92010

[21] Appl. No.: 563,277

[22] Filed: Dec. 19, 1983

[51] Int. Cl.[3] ..... A01H 5/00

[52] U.S. Cl. ..... Plt./7

[58] Field of Search ..... Plt./7

*Primary Examiner*—Robert E. Bagwill

[57] ABSTRACT

The subject of the present disclosure is a new and distinct variety of miniature rose plant characterized by it's petals of pale pink with slightly darker pink at the margins.

1 Drawing Figure

1

The present invention relates to a new and distinct variety of a hardy, dwarf, miniature bush plant of the miniature class; the variety being primarily characterized as a pink blend.

The variety is further characterized by:

Long stemmed blooms, borne singly or in sprays, held very erect and well above the foliage.

Has a very slight fragrance.

The plant ranges in height from 12 to 24 inches. The canes are sturdy and erect, heavily branched with medium foliage covering. The plant is a moderate to heavy bloomer that does well in either the green house or outdoors.

The plant is very vigorous with good growth habits, well shaped and attractive in appearance, bearing numerous leaflets of average size.

The seed parent was an unnamed seedling of unknown parentage, and the pollen parent was Coral Treasure (Miniature Rose Plant, orange blend; R. S. Moore; introduced by Sequoia Nursery, 1971).

Subsequent to the origination of the variety, I have successfully reproduced it at TINY PETALS NURSERY located at aforesaid retaining the distinguishing characteristics through succeeding propagations by cuttings.

The descriptive matter which follows pertains to roses grown and color values observed in plants and newly opened blooms in the months of May and June. The plants were grown outdoors in Chula Vista, Calif., and are believed to be accurate standards for this same cultivar in similar conditions of soil and climate elsewhere.

The color photograph illustrates the variety.

Referring now specifically to the new and distinct variety of miniature rose plant, the following is a detailed description thereof in outline; all major color plate identifications being by reference to the British Colour Council Horticultural Colour Chart, except where common terms of color definition are employed.

Type: Hardy, dwarf, bushy, green house or outdoor, garden decoration and exhibition-quality potted plant.

Class: Miniature.

Variety name: Cupie doll.

Flowers borne: One to a stem or in aprays of 3 to 5 or more on erect stems with foliage well below the blooms.

Quantity of bloom: Moderate to heavy both outdoors and green house grown.

2

Bud:

*Peduncle.*—Short to medium (averaging 15 to 30 mm); average diameter and sturdy; medium green with light to occasionally heavy tinting of bronze.

*Hairs.*—Extremely small and delicate; very numerous; bronze in color; located over the entire surface of the peduncle and outer surface of sepals but not on the calyx tube.

*Calyx.*—Color is Pod Green (061/1 page 120) with tinting of bronze that varies from slight to very heavy.

*Opening.*—Opens well in all weather.

Bloom:

*Size when fully open.*—Average for a miniature variety 40 to 45 mm (1¾").

*Petalage.*—Double — Averaging 20 to 30 petals, arranged regularly plus petaloids (10 to 15 or more).

*Form.*—Urn-shaped to ovoid as the bloom progresses. The petals remain at first tightly cupped with the tips and/or margins reflexed outward, becoming later at maturity more loosely cupped. At the fully opened stage, the outer rows of petals reflex at their margins, rolling under from the apex of the petal on both sides.

Petals: Fairly thick with good substance and a matte finish.

*Shape.*—Outer petals are of a broad obovate form with a slight peak at the apex. The intermediate petals are very much like the outer petals only narrower. The inner petals are narrower obovate form; very little difference between intermediate and inner petals is noticeable. The petaloids are like small lanceolates with occasional irregularities in shape.

Color: Newly opened flowers from plants grown outdoors (June and July 1983), Chula Vista, Calif.:

*Outside petals.*—Upper surface — Azalea Pink (618/2 page 74) with an occasional apex of Azalea Pink (618 page 74) and a narrow base of Naples Yellow (403/2 page 121).

*Outside petals.*—Under surface — Azalea Pink (618/3 page 74) with a margin of Carmine Rose (621 to 621/1 page 75) and a narrow base of Naples Yellow (403/2 page 121).

*Intermediate petals.*—Upper surface — Azalea Pink (618/3 page 74) with a base of Naples Yellow (403/2 page 121).

*Intermediate petals.*—Under surface — Azalea Pink (618/3 page 74) with a margin of Carmine Rose (621 to 621/1 page 75) and a base of Naples Yellow (403/2 page 121).

*Inner petals.*—Upper surface — Azalea Pink (618/2 page 74) with a broad base of Naples Yellow (403/2 page 121).

*Inner petals.*—Under surface — Azalea Pink (618/2 page 74) with a margin of Carmine Rose (621 to 621/1 page 75) and a base of Naples Yellow (403/2 page 121).

*All petals.*—The tip of the petals where they attach to the calyx is Naples Yellow (403 page 121).

Reproductive organs:

*Stamens.*—A generous amount arranged uniformly around the pistil.

*Filament.*—Short to medium in length; pale yellow in color.

*Pollen.*—Abundant.

*Pistil.*—Average length, abundant and spreading.

*Styles.*—Average to long; pale yellow in color.

*Ovaries.*—All encased in the calyx.

*Hips.*—Some.

*Seed.*—Few or none.

*Sepals.*—Permanent; lanceolate-shaped; open as the bloom opens, but do not recurve against the peduncle.

Foliage:

*Leaves.*—Five to seven, average size for a miniature rose plant.

*Leaflets.*—Broad ovate-shaped.

*Margin.*—Very serrated with occasional reddish tinge on the edge, usually present on the newer foliage.

*Color.*—Ranging from Scheeles Green (860 page 175) to Spinach Green (0960/2 page 187). The upper surfaces are satiny and the under surfaces are matte finish with a slightly lighter color than the upper surface.

*Rachis.*—Medium strength; upper surface may have a few small hairs; grooved. Under side smooth except for a few sparse thorns.

*Stipules.*—Varying in length from medium to long; average width; tapering auricles angled outward at about 45 degrees.

Growth:

*Habit.*—Dwarf; bushy; much branched; average to large for a miniature rose plant.

*Growth.*—Vigorous.

*Canes.*—Medium; sturdy; held very erect.

*Main stems.*—Color — Spinach Green (0960/2 page 187) to Spinach Green (0960/3 page 187) with occasional tinting of bronze on the more mature stems.

*Thorns.*—None on the main stems or branches, with only a few very small thorns located on the underside of the rachis, which are very sparse when present at all. Color — Pale yellow to pale green.

*Branches.*—Color — Spinch Green (0960/2 page 187) to Spinach Green (0960/3 page 187) with occasional tinting of bronze. Medium to long in length; sturdy; very erect. No thorns, prickles or hairs present.

The miniature rose plant and its flowers as herein described may vary in slight detail due to climatic, soil, and cultural conditions under which the variety may be grown; the present description being of the variety as grown at Chula Vista, Calif. cm The following is claimed:

1. A new and distinct variety of miniature rose plant of hardy, dwarf, bushy, much branched habit, substantially as illustrated and described, characterized by its petals of pale pink with slightly darker pink at the margins and vigorous growth habit, easy to propagate from cuttings, with flowers borne singly and in sprays of 3 to 5 or more.

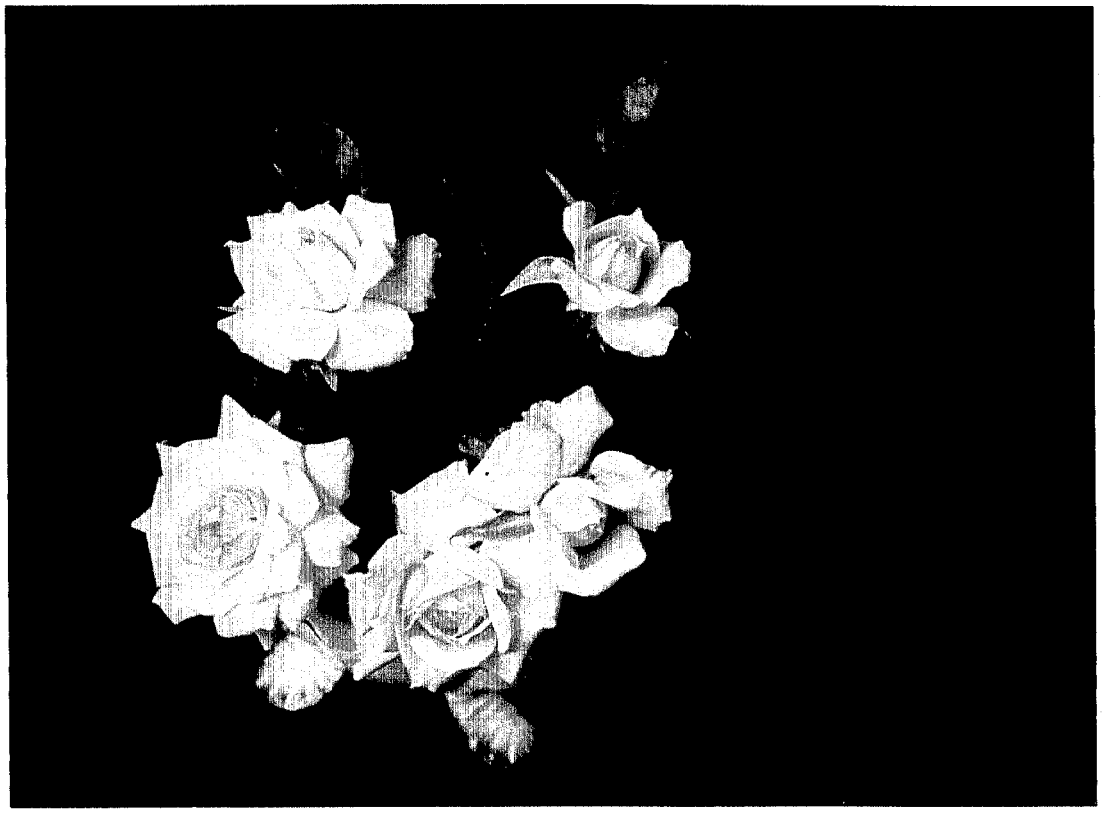

* * * * *